US006753184B1

(12) United States Patent
Moreton et al.

(10) Patent No.: US 6,753,184 B1
(45) Date of Patent: Jun. 22, 2004

(54) HUMIDITY INDICATORS

(75) Inventors: Stephen Moreton, Cheshire (GB); Graham J Earl, Cheshire (GB)

(73) Assignee: Ineos Silicas Limited, Warrington (GB)

( * ) Notice: Subject to any disclaimer, the term of this patent is extended or adjusted under 35 U.S.C. 154(b) by 0 days.

(21) Appl. No.: 09/959,121

(22) PCT Filed: Apr. 12, 2000

(86) PCT No.: PCT/GB00/01390

§ 371 (c)(1),
(2), (4) Date: Oct. 22, 2001

(87) PCT Pub. No.: WO00/65339

PCT Pub. Date: Nov. 2, 2000

(30) Foreign Application Priority Data

Apr. 22, 1999 (GB) ............................................. 9909219

(51) Int. Cl.[7] ........................ G01N 21/77; G01N 33/18
(52) U.S. Cl. .......................... 436/39; 436/84; 436/164; 436/166; 436/169; 422/55; 422/56; 73/29.01; 73/29.04
(58) Field of Search ............................ 436/39, 84, 164, 436/166, 169; 422/55, 56; 73/29.01, 29.04

(56) References Cited

U.S. PATENT DOCUMENTS

| | | | | |
|---|---|---|---|---|
| 2,460,065 A | * | 1/1949 | Davis | 436/41 |
| 2,460,071 A | * | 1/1949 | Davis | 436/41 |
| 3,597,263 A | * | 8/1971 | Bancroft et al. | 422/56 |
| 3,953,514 A | * | 4/1976 | Yamazaki et al. | 568/354 |
| 3,966,830 A | * | 6/1976 | Shimada et al. | 568/937 |
| 4,098,120 A | * | 7/1978 | Manske | 116/200 |
| 5,290,516 A | * | 3/1994 | Greco et al. | 422/57 |

FOREIGN PATENT DOCUMENTS

| | | |
|---|---|---|
| DE | 1952539 | 4/1971 |
| SU | 568894 | 8/1977 |
| SU | 989479 | 1/1983 |

OTHER PUBLICATIONS

Lopez, T. et al., "Spectroscopic study if sol–gel silica dropped with iron ions", Materials Chemicals and Physics, vol. 30, No. 3, Jan. 1992 pp. 161–167.

Belotserkovskaya N.G. et al., "Indicator properties of cobalt silica gels obtained by introduction of cobalt salts into silica sols and silica gels", Russian Journal of Applied Chemistry, vol. 62, No. 10(1), Oct. 1, 1989, pp. 203–2040.

* cited by examiner

*Primary Examiner*—Maureen M. Wallenhorst
(74) *Attorney, Agent, or Firm*—Mayer Brown Rowe & Maw LLP

(57) ABSTRACT

Silica-based carrier impregnated with iron(III) or iron(II) salts functions as a humidity indicator giving a yellow/amber to nearly colourless colour change as the carrier humidifies.

19 Claims, No Drawings

HUMIDITY INDICATORS

This application is the National Phase of International Application PCT/GB00/01390 filed Apr. 12, 2000 which designated the U.S. and that International Application was published under PCT Article 21(2) in English.

This invention relates to silica-based humidity indicators.

Cobalt chloride indicator gels are used in a range of applications, e.g. to indicate moisture change in gas drying columns. Other drying applications include their use in transformer breathers, tank breathers, in the protection of electronics and telecommunication systems and in laboratory desiccators. It is estimated that approximately 2000 tonnes of cobalt chloride indicator gel are used annually on a global basis.

Cobalt-containing gels for use as humidity indicators have been disclosed in U.S. Pat. Nos. 2,460,071 (disclosing cobalt chloride), 2,460,069 (disclosing cobalt bromide), 2,460,073 (disclosing cobalt iodide), 2,460,074 (disclosing cobalt thiocyanate), 2,460,065 (disclosing cobalt sulphate) and 2,460,070 (disclosing cobalt phosphate).

Indicator silica get is currently produced by impregnating humidified silica-gel or a silica hydrogel with a cobalt chloride solution to produce a dry granular end-product which contains a minimum of 0.5% cobalt chloride and which is blue in colour, changing to pink when water has been adsorbed. Humidified gel is silica gel that has been saturated with water from the vapour phase in order to avoid decrepitation upon impregnation. If the cobalt chloride solution is added directly to the dried gel, the grain size is reduced.

Cobalt chloride has recently been classified as a Category 2 carcinogen (notification from the EEC, Dec. 15, 1998) with the consequence that the use of cobalt chloride indicator gel in industrial applications will require much tighter control to ensure exposure limits are strictly controlled. If acceptable alternatives to the cobalt chloride indicator gel were not available to indicate when saturation had occurred in gas/air drying applications, for instance, this could have serious implications on the users' downstream processes, e.g. corrosion through moisture damage.

U.S. Pat. Nos. 2,460,072 and 2,460,067 also disclose copper(II) chloride and copper(II) bromide, respectively; but these compounds are not considered suitable candidates for a commercial silica gel-based humidity indicator because of potential toxicity and environmental considerations.

It has been demonstrated that the vanadium compound $VOCl_3$, when impregnated into silica gel gives a colour change from colourless to yellow to orange to red to brown as humidity increases—see the following references:

Belotserkovskaya et al., "Indicator properties of vanadium-modified silicas and zeolites" Zh. Prikl. Khim. (Leningrad), 63(8), 1674–9;

Malygin, A. A. "Synthesis and study of physicochemical properties of vanadium-containing silica—a humidity indicator", Sb. Nauch. Tr. VNII Lyuminoforov I Osobo-Chist. Veshchestv, 23, 24–8; and Malygin, A. A. et at, "Study of properties of vanadium-containing silica gel", Zh. Prikl. Khim. (Leningrad), 52(9), 2094–6.

However, $VOCl_3$ is corrosive, toxic and difficult to prepare and handle.

The present invention therefore addresses the problem of producing an alternative, safe indicator gel to those which are cobalt-based or contain a transition metal salt which is considered to be toxic.

According to one aspect of the present invention there is provided a humidity indicator compound comprising a silica-based carrier containing an iron(II) and/or iron(III) salts or salts as the active indicator.

A second aspect of the present invention resides in the use as a humidity indicator of a compound comprising silica-based carrier containing an iron(II) and/or iron(III) salt or salts as the active indicator.

According to a third aspect of the present invention there is provided a method of monitoring the humidity level within an atmosphere comprising exposing a dried silica-based carrier containing an iron(II) and/or iron(III) salt or salts to said atmosphere and observing colour changes therein.

Typically, humidified silica gel is used as the carrier; however other forms of silica may be used in the production of the silica-based carrier, e.g. silica hydrogel or dry silica gel. The silica-based material may have any of the physical forms normally available. In particular, the form can be irregular granules or approximately spherical beads (often called spherical or beaded silica gel).

The presence of the iron salt imparts a yellow or amber colour to the dry silica-based carrier. When the indicator is exposed to moisture, it then adsorbs water and the colour is observed to fade until it becomes almost colourless when the silica-based carrier is almost saturated with water. This effect has been observed to be a general effect for those iron salts which have been examined.

Once the extent of exposure of the indicator to moisture has resulted in a change of colour from yellow/amber to almost colourless the silica-based carrier may be processed, e.g. by heating to restore its colour, and re-used for humidity monitoring.

The effect referred to above, i.e. colour change from yellow or amber to almost colourless, has been observed in all iron salts examined, e.g. simple iron salts such as ferric sulphate, ferric chloride or ferric nitrate and salts having at least two cations of which one is iron(II) or iron(III), examples of which are ammonium iron(III) sulphate, ammonium iron(II) sulphate and potassium iron(III) sulphate. The effect has been found to be particularly pronounced for the double sulphates or alums.

While not wishing to be bound by theory, the effect is thought to be related to hydrolysis and formation of coloured, polymeric Fe-hydroxy species. In dry silica, such species are thought to be polymerised, and also bound to the silica, to a greater extent than in humidified gel. The higher the degree of polymerisation, and possibly also bonding to the silica, the more intense the colour.

The effect would appear to be related to pH. Those iron salts which exhibit higher pH values when dissolved in water give more intense colours, and more pronounced colour changes, than those which exhibit lower (i.e. more acidic) pH values possibly due to a higher degree of polymerisation of the Fe-hydroxy complexes. Thus ammonium iron(III) sulphate at 10% by weight in water has a pH of 1.7 and produces a silica-based carrier with a deep amber colour, whereas a 10% solution of ferric chloride has a pH of 1.3 and results in a paler yellow shade. The colour of the simple salts can be enhanced by adjusting the pH to higher values comparable to the alums. This may be achieved by the addition of small amounts of sodium hydroxide solution.

Normally an iron(III) salt is employed; however, ferrous counterparts of the ferric salts may also be used since the ferrous ion readily oxidises to the ferric state.

Typically, the silica gel used has a BET surface area in the range of 200 to 1500 $m^2/g$. The pore volume of silica gel may be in the range of 0.2 to 2.0 ml/g, as measured by nitrogen absorption. For example, Sorbsil desiccant gel (Sorbsil is a Trade Mark of Crosfield Limited) typically has a surface area of about 800 m²/g and a pore volume of about 0.4 ml/g. Surface area is determined using standard nitrogen adsorption methods of Brunauer, Emmett and Teller (BET).

The amount of iron present in the silca-based carrier is preferably at least about 0.01 per cent by weight of iron, determined as Fe, relative to the dry weight of the carrier, typically up to about 2.0 percent and usually in the range of about 0.01 percent to about 1.0 percent by weight of the dry weight of the silica-based carrier. The dry weight of a prepared humidity indicator, based on silica gel, according to the invention can be determined by placing a weighed sample (approx. 20 grams) in an oven at 145° C. for 16 hours and then weighing the dried material.

According to another aspect of the present invention there is provided a method of producing a humidity indicator comprising soaking silica-based carrier with a solution of an iron(II) and/or iron(III) salt to secure impregnation of the carrier and drying the impregnated carrier.

Typically the indicator gel is prepared by contacting the silica-based carrier with a solution of iron salt containing 1 percent by weight or higher (up to the saturation point) of the iron salt, e.g. by soaking humidified white silica gel in the iron salt solution. Humidified gel is preferred, but the use of dry gel is acceptable. When dry gel is used, the granules decrepitate, so that the product has a smaller particle size than the original product, but, generally, the particle size is still satisfactory for use as a drying agent. In the case of ammonium iron(III) sulphate (herein referred to as iron(III) alum), the solution may range from 1 percent to approximately 50 percent by weight (saturation at 25° C.), or higher at higher temperatures. Preferably, the solution contains 10 to 40 percent by weight iron(III) alum at 25° C. The use of a high concentration of iron salt helps to reduce the processing time for preparing the indicating silica-based product. The gel is typically soaked in the solution for a period of from 10 minutes to 10 days, preferably 1 to 30 hours, more preferably 2 to 24 hours. The excess solution is drained and the gel dried at 105 to 230° C. whereupon it develops its amber colour. An impregnated product dried in this manner will usually have a weight loss after heating at 145° C. for 16 hours of less than 10 percent by weight Preferably, the weight loss at 145° C. is less than 2 percent by weight.

The invention is illustrated by the following, non-limiting examples.

EXAMPLE 1

Sorbsil silica gel (commercially available from Crosfield Limited of Warrington, England) was exposed to humidity or steam until the pore system was totally saturated with water transported from the vapour phase. 50 g of this humidified gel was impregnated with a ferric salt by soaking the gel in 200 ml of 20 percent by weight iron(III) alum solution for 24 hours. The gel was drained and then dried at 145° C. for 16 hours. 6 g samples of the impregnated dried gel were placed in a series of glass tubes and air at various levels of relative humidity (RH) passed through the gel for 7 hours at a flow rate of 4 litres/minute. After exposure to moisture containing air for this length of time, the colour of the gel samples was measured using a Minolta CR200 Chromameter, calibrated to a standard white plate and using CIE Illuminant C and a 2° observer angle. The results, expressed according to the $L^*$, $a^*$, $b^*$ system, are given in Table 1 below.

TABLE 1

| % RH | % weight gain | $L^*$ | $a^*$ | $b^*$ |
| --- | --- | --- | --- | --- |
| 0 | 0.0 | 39.96 | 10.96 | 32.38 |
| 20 | 8.4 | 44.40 | 8.95 | 35.47 |
| 40 | 14.9 | 48.13 | 4.39 | 23.53 |
| 50 | 18.2 | 50.00 | 1.67 | 15.90 |
| 80 | 25.6 | 59.94 | −0.30 | 12.30 |

The increase in lightness ($L^*$) and decrease in redness ($a^*$) and yellowness ($b^*$) is apparent from the above data and is readily observed visually, allowing an obvious indication of when the gel has become saturated with moisture. Visually, the gel appears almost colourless after exposure to 50% RH air at 4 litres/min for 7 hours.

EXAMPLE 2

A further batch of silica gel was prepared according to the method of Example 1 and the gel was soaked in the ferric alum solution for 4 hours, rather than 24 hours. The product was similarly exposed to moist air and the results are given in Table 2 below.

TABLE 2

| % RH | Colour | % weight gain | $L^*$ | $a^*$ | $b^*$ |
| --- | --- | --- | --- | --- | --- |
| 0 | Deep amber | 0.0 | 40.77 | +13.23 | 35.13 |
| 20 | Pale amber | 11.7 | 45.62 | +6.94 | 36.90 |
| 40 | Yellow | 20.6 | 56.48 | +0.59 | 23.94 |
| 50 | Pale Yellow | 25.4 | 53.64 | −0.28 | 17.90 |
| 80 | Almost colourless | 31.0 | 57.93 | −1.74 | 14.28 |

This product shows an improvement over Example 1 especially in terms of water adsorption capacity.

EXAMPLE 3

Examples of ferric salts were placed in the oven at 145° C. for 16 hours to observe the effect of dehydration and to see if any colour changes observed matched those obtained with silica-based carriers impregnated with the ferric salts. Observations are given below in Table 3.

TABLE 3

| Salt | Colour prior to drying | Colour after drying |
| --- | --- | --- |
| Ferric alum | pale lilac | light buff |
| Ferric sulphate | light buff | light buff |
| Ferric chloride | deep yellow | dark brown (decomposed to ferric oxide) |
| Ferric nitrate | pale violet | dark brown (decomposed to ferric oxide) |

Where colour changes were observed, it was found that they did not correspond to those seen in the impregnated carrier. This indicates that the colour change observed in the carrier impregnated with iron(III) salts is not due to a simple hydration/rehydration effect as with cobalt and copper salts.

EXAMPLE 4

Silica gel was impregnated with various iron salts using a similar method to that described in Example 1. The details of the reaction conditions are given in Table 4 below. In these laboratory experiments particular care was taken to remove as much excess solution as possible from the gel using tissue before the oven drying. During oven drying the treated materials were spread in as thin a layer as possible. This was found to give a product with a more homogenous colour.

TABLE 4

| Sample | Iron salt | Solution strength | Ratio gel/solution | Soaking time |
|---|---|---|---|---|
| A | Potassium iron alum | 10% | 50 g/200 ml | 24 hours |
| B | Ferric sulphate | 40% | 50 g/200 ml | 24 hours |
| C | Ferric chloride | 10% | 100 g/200 ml | 2.5 hours |
| D | Ferric nitrate | 10% | 100 g/200 ml | 2.5 hours |

The samples were exposed to moist air as described in Example 1 and the results are given in Table 5 below.

TABLE 5

| Sample | % RH | % moisture | Colour | L* | a* | b* |
|---|---|---|---|---|---|---|
| A | 0 | 0 | Amber | 50.97 | +7.54 | +35.06 |
|   | 20 | 10.5 | Amber | 49.55 | +6.61 | +34.73 |
|   | 40 | 20.9 | Yellow | 54.34 | +2.00 | +25.10 |
|   | 50 | 23.6 | Almost colourless | 59.63 | −0.23 | +17.80 |
|   | 80 | 26.1 | Almost colourless | 60.20 | +0.29 | +18.02 |
| B | 0 | 0 | Yellow/amber | 41.94 | +4.15 | +29.37 |
|   | 20 | 11.0 | Yellow | 53.22 | +2.55 | +30.21 |
|   | 40 | 19.4 | Yellow | 53.75 | +1.32 | +27.22 |
|   | 50 | 21.5 | Pale yellow | 57.67 | +1.14 | +26.74 |
|   | 80 | 23.8 | Almost colourless | 55.01 | −0.32 | +22.54 |
| C | 0 | 0 | Amber | 39.02 | +10.12 | +32.63 |
|   | 20 | 11.2 | Yellow/amber | 48.05 | +4.20 | +28.30 |
|   | 40 | 23.5 | Pale yellow/amber | 52.35 | +2.88 | +25.76 |
|   | 50 | 27.1 | Pale yellow/amber | 54.62 | +1.79 | +23.67 |
|   | 80 | 31.5 | Pale yellow/amber | 55.45 | +1.46 | +23.29 |
| D | 0 | 0 | Amber | 44.49 | +7.17 | +31.10 |
|   | 20 | 10.8 | Pale amber | 45.79 | +6.47 | +29.90 |
|   | 40 | 23.2 | Pale amber | 53.71 | +4.14 | +28.64 |
|   | 50 | 26.6 | Pale amber | 51.47 | +3.62 | +26.16 |
|   | 80 | 29.6 | Pale yellow | 53.74 | +2.68 | +25.34 |

The chloride and nitrate show a less marked colour change than when alum is used. Nevertheless some lightening of colour is visible to the human eye and the trend can still be the L*a*b* system.

EXAMPLE 5

50 g of humidified gel prepared as in Example 1 was soaked in 200 ml of a 20 percent by weight of ammonium iron(II) sulphate for 4 hours and dried as in Example 1. The product was exposed to moist air as in Example 1 and the observed colour changes are shown in Table 6 below.

TABLE 6

| % RH | % water absorbed | Colour | L* | a* | b* |
|---|---|---|---|---|---|
| 0 | 0 | Amber | 44.09 | +15.81 | +43.11 |
| 20 | 11.4 | Amber | 44.97 | +14.44 | +40.84 |
| 40 | 23.4 | Pale amber | 52.82 | +8.43 | +36.41 |
| 50 | 26.6 | Pale yellow/amber | 52.05 | +6.08 | +32.99 |
| 80 | 30.0 | Pale yellow | 57.91 | +2.62 | +27.56 |

Ammonium iron(II) sulphate has the normal green colour of ferrous salts. However, silica gel impregnated with it and dried has the amber colour associated with iron(III) salts.

EXAMPLE 6

Samples of commercially available beaded silica gel from three suppliers were humidified and then impregnated with 20% iron(II) alum solution for 7 hours, dried at 145° C. overnight and the colour recorded. Samples were then placed in a desiccator at 100% relative humidity for a week and the colour recorded.

The desiccant silica gel beads used in this experiment, and their suppliers, were:

| Bead type/size | Supplier |
|---|---|
| "TS6", 2-5 mm | OingDao HaiYang Chemical Group Co. Ltd., 7 Mian Yang Road, OingDao, China. |
| 2-5 mm | Silgel Packaging Ltd., 2 Horton Court, Hortonwood 50, Telford, Shropshire, U.K. |
| Ca. 1-3 mm | Engelhard Corp., 600 E. McDowell Road, Jackson, MS 39204, U.S.A. |

Colour changes for the desiccant beaded silica gel impregnated with iron(III) alum are given in Table 7 below.

TABLE 7

| Supplier | | Colour | L* | a* | b* |
|---|---|---|---|---|---|
| Haiyang | before exposure | Amber | 46.05 | +10.10 | +37.91 |
|  | after exposure | Almost colourless | 53.10 | −1.58 | +18.05 |
| Silgel | before exposure | Amber | 48.69 | +13.64 | +43.57 |
|  | after exposure | Almost colourless | 61.07 | −2.16 | +16.04 |
| Engelhard | before exposure | Amber | 50.27 | +16.18 | +51.36 |
|  | after exposure | Almost colourless | 58.03 | −1.35 | +15.50 |

In each case the beaded silica gel shows a pronounced-colour change from amber when dry to almost colourless when humidified. This is the same behaviour as is observed when an irregular granular silica gel is used.

EXAMPLE 7

Dry silica gel, when placed in water (or an aqueous solution), is known to decrepitate. However, decrepitation is not necessarily a problem in the preparation of acceptable indicating silica gel. To demonstrate this, 50 g dry silica gel having a size range of approximately 2.5 to 6.0 mm was soaked in 200 ml of 20 percent by weight iron(III) alum solution for 4 hours and then dried at 145° C. overnight. The colour of the resulting gel was measured before and after being left in a desiccator at 100% relative humidity for 3 weeks. The colour changes are shown in Table 8 below. A sieve analysis was carried out before and after the impregnation step to demonstrate the effect of decrepitation on particle size distribution. The results are shown in Table 9 below.

TABLE 8

| | Colour | L* | a* | b* |
|---|---|---|---|---|
| before exposure | Amber | 58.32 | +9.97 | +53.29 |
| after exposure | Pale yellow | 66.67 | −2.84 | +20.06 |

TABLE 9

| Particle size (mm) | Weight % before impregnation | Weight % after impregnation |
|---|---|---|
| <5.6 | 4.74 | 0.00 |
| 3.55–5.6 | 63.31 | 0.71 |
| 1.6–3.55 | 31.91 | 36.17 |
| 1.0–1.6 | 0.04 | 36.35 |
| 0.5–1.0 | 0.01 | 22.40 |
| <0.5 | 0.00 | 4.37 |

There had been some breakdown in particle size as a result of the decrepitation but this does not interfere with the humidity indication. The gel in this example still showed the expected amber to nearly colourless colour change and the particle size distribution was still acceptable for normal desiccant use.

EXAMPLE 8

100 kg of humidified 2.5–6.0 mm silica gel prepared as in Example 1 was soaked in 180 litres of 20 percent by weight iron(III) alum solution for 4 hours. A pump was used to keep the solution circulating at a rate of between 25 and 50 litres per minute. The gel was then withdrawn, allowed to drain and then dried at 150° C. overnight in 2 cm deep trays in an oven. Colour and adsorption capacity were measured for the fresh material as in Example 1. Analysis showed it to contain 0.34% Fe.

200 g of orange indicator gel, made as described above, were placed in a bowl in a desiccator containing water. The relative humidity in this desiccator was nearly 100% at 25° C. After about two weeks exposure to this high humidity the gel had decolourised. It was then oven dried at 145° C. overnight and the process repeated. This exposure and regeneration was carried out ten times. After the ten cycles of humidifying and drying the colour and adsorption capacity of the gel were measured again as in Example 1 and compared to the original material. The results are shown below in Tables 10 and 11.

TABLE 10

Effect on colour.

| Sample | | L* | a* | b* |
|---|---|---|---|---|
| Fresh | before exposure | 42.80 | +11.28 | +37.71 |
| | after exposure | 61.92 | −1.02 | +15.18 |
| After 10 cycles | before exposure | 41.74 | +11.48 | +37.86 |
| | after exposure | 56.72 | −1.64 | +12.58 |

TABLE 11

Effect on adsorption capacity.

| Sample | % RH | % water adsorbed |
|---|---|---|
| Fresh | 20 | 11.6 |
| | 40 | 22.9 |
| | 50 | 28.0 |
| | 80 | 31.2 |
| After 10 cycles | 20 | 10.1 |
| | 40 | 22.5 |
| | 50 | 27.6 |
| | 80 | 30.8 |

Visually, the fresh and regenerated gels were indistinguishable. There had been no deterioration in colour shade, intensity or distribution and the colour change effect was also unaffected. In addition, the adsorption capacities show no adverse change after ten regeneration cycles.

Similar recycle results can be obtained with other iron salts but it has been found that the drying temperature may need to be kept below about 100° C. when certain salts (e.g. $FeCl_3$) are used, in order to avoid the development of an uneven colouration.

What is claimed is:

1. A humidity indicator comprising a silica gel carrier impregnated with an active indicator consisting essentially of an iron(II) and/or iron(III) salt or salts, the iron salt being a salt containing more than one cation of which one is iron(II) or iron(III).

2. A humidity indicator comprising a silica gel carrier containing an iron(II) and/or iron(III) salt or salts as an active indicator, the iron salt being a salt containing more than one cation of which one is iron(II) or iron(III), wherein, upon exposure to a humid environment the indicator will undergo a color change and whereinafter the indicator may be regenerated for re-use.

3. An indicator as claimed in claim 2 in which the iron salt is ammonium iron(III) sulphate, ammonium iron(II) sulphate or potassium iron(III) sulphate.

4. An indicator as claimed in claim 2 in which the iron(II) or iron(III) salt is present in an amount in the range 0.01 percent to 2.0 percent by weight expressed as Fe based upon weight of dry carrier.

5. A humidity indicator as claimed in claim 2 in which the silica gel is humidified silica gel.

6. A humidity indicator as claimed in claim 2 in which the silica gel is beaded or granular silica gel.

7. A method of monitoring the humidity level within an atmosphere comprising exposing a dried silica gel carrier containing an iron(II) and/or iron(III) salt or salts to said atmosphere and observing colour changes therein, the iron salt being a salt containing more than one cation of which one is iron(II) or iron(III), and wherein the color of the iron salt may be regenerated, thereby allowing the silica gel to be re-used.

8. A method as claimed in claim 7 in which the iron salt is ammonium iron(III) sulphate, ammonium iron(II) sulphate or potassium iron(III) sulphate.

9. A method of producing a humidity indicator comprising soaking silica gel carrier with a solution of an iron(II) and/or iron(III) salt or salts to impregnate the carrier and drying the impregnated carrier, the iron salt being a salt containing more than one cation of which one is iron(II) or iron(III), and wherein, upon exposure to atmospheric humidity, the humidity indicator will undergo a color change and wherein following the color change heating the humidity indicator allows the indicator to be re-used.

10. A humidity indicator in the form of an iron impregnated silica gel carrier produced by the method as claimed in claim 9.

11. A humidity indicator comprising a silica gel carrier containing an iron(II) and/or iron(III) salt or salts as an active indicator, the iron salt being a salt containing more than one cation of which one is iron(II) or iron(III) and imparting a color to the silica gel, wherein, upon exposure to a humid environment the color of the silica gel fades.

12. A humidity indicator according to claim 11, wherein the iron salt imparts a yellow color to the silica gel.

13. A humidity indicator according to claim 11, wherein the iron salt imparts an amber color to the silica gel.

14. A method of producing a humidity indicator comprising imparting a color to a silica gel carrier by soaking the silica gel carrier with a solution of an iron(II) and/or iron(III)

salt or salts to impregnate the carrier and drying the impregnated carrier, the iron salt being a salt containing more than one cation of which one is iron(II) or iron(III), and wherein, upon exposure to atmospheric humidity, the color of the humidity indicator will substantially fade.

15. A method according to claim 14, wherein the iron salt imparts a yellow color or an amber color to the carrier and wherein the color will substantially fade upon absorption of atmospheric moisture and wherein the color may be substantially regenerated by heating the humidity indicator.

16. A method of monitoring the humidity level within an atmosphere comprising exposing a humidity indicator comprising dried silica gel carrier containing an iron(II) and/or iron(III) salt or salts which imparts a color to the carrier to said atmosphere and observing color changes in the carrier, the iron salt being a salt containing more than one cation of which one is iron(II) or iron(III), and, regenerating the humidity indicator for re-use thereof.

17. A method according to claim 16, wherein the color imparted to the carrier by the iron salt is a yellow or an amber color, and which comprises exposing the humidity indicator to atmospheric moisture for a time sufficient to cause fading of the color of the carrier imparted by the iron salt to at least substantially colorless.

18. A method according to claim 17, further comprising heating the humidity indicator after said time to regenerate a yellow or amber color in the carrier and re-using the regenerated humidity indicator to monitor the humidity level within an atmosphere.

19. A method according to claim 18, which comprises repeating the steps of exposing and heating at least two times.

* * * * *